US009359649B2

(12) United States Patent
Lloyd, Jr. et al.

(10) Patent No.: US 9,359,649 B2
(45) Date of Patent: *Jun. 7, 2016

(54) METHODS FOR COLLECTION, STORAGE AND TRANSPORTATION OF BIOLOGICAL SPECIMENS

(71) Applicant: ViveBio, LLC, Alpharetta, GA (US)

(72) Inventors: Robert M. Lloyd, Jr., Suwanee, GA (US); Darrell A. Burns, Dacula, GA (US); Joe T. Huong, Norcross, GA (US)

(73) Assignee: VIVEBIO, LLC, Alpharetta, GA (US)

( * ) Notice: Subject to any disclaimer, the term of this patent is extended or adjusted under 35 U.S.C. 154(b) by 97 days.

This patent is subject to a terminal disclaimer.

(21) Appl. No.: 14/165,877

(22) Filed: Jan. 28, 2014

(65) Prior Publication Data

US 2014/0141411 A1    May 22, 2014

Related U.S. Application Data

(60) Continuation of application No. 12/482,907, filed on Jun. 11, 2009, now Pat. No. 8,685,748, which is a division of application No. 11/061,698, filed on Feb. 18, 2005, now Pat. No. 7,638,099.

(60) Provisional application No. 60/561,037, filed on Apr. 9, 2004.

(51) Int. Cl.
| | |
|---|---|
| *G01N 1/18* | (2006.01) |
| *C12Q 1/70* | (2006.01) |
| *C12M 1/00* | (2006.01) |
| *B01L 3/00* | (2006.01) |

(52) U.S. Cl.
CPC ............... *C12Q 1/70* (2013.01); *B01L 3/50825* (2013.01); *C12M 45/22* (2013.01); *B01L 3/502* (2013.01); *B01L 2200/185* (2013.01); *B01L 2300/042* (2013.01); *B01L 2300/046* (2013.01); *B01L 2300/047* (2013.01); *B01L 2300/069* (2013.01); *B01L 2300/105* (2013.01); *Y10T 436/108331* (2015.01); *Y10T 436/255* (2015.01); *Y10T 436/2575* (2015.01); *Y10T 436/25375* (2015.01); *Y10T 436/25625* (2015.01)

(58) Field of Classification Search
CPC ............ B01L 2200/16; B01L 2200/18; B01L 3/5029; G01N 1/30; G01N 1/286
USPC .................................. 436/179, 180, 177, 178
See application file for complete search history.

(56) References Cited

U.S. PATENT DOCUMENTS

| | | |
|---|---|---|
| 3,418,079 A | 12/1968 | Rey et al. |
| 3,616,259 A | 10/1971 | Buetler |
| 3,888,629 A | 6/1975 | Bagshawe |
| 4,014,748 A | 3/1977 | Spinner et al. |
| 4,299,916 A | 11/1981 | Litman et al. |
| 4,455,370 A | 6/1984 | Bartelsman et al. |
| 4,677,054 A | 6/1987 | White et al. |
| 4,789,630 A | 12/1988 | Bloch et al. |
| 4,789,639 A | 12/1988 | Fleming |
| 4,895,795 A | 1/1990 | Frazier et al. |
| 4,965,190 A | 10/1990 | Woo et al. |
| 5,057,410 A | 10/1991 | Kawasaki et al. |
| 5,089,387 A | 2/1992 | Tsay et al. |
| 5,092,466 A | 3/1992 | Anderson |
| 5,143,627 A | 9/1992 | Lapidus et al. |
| 5,163,441 A | 11/1992 | Monthony et al. |
| 5,188,963 A | 2/1993 | Stapleton |
| 5,281,516 A | 1/1994 | Stapleton et al. |
| 5,346,672 A | 9/1994 | Stapleton et al. |
| 5,382,511 A | 1/1995 | Stapleton |
| 5,432,097 A | 7/1995 | Youmo |
| 5,436,129 A | 7/1995 | Stapleton |
| 5,451,500 A | 9/1995 | Stapleton |
| 5,494,646 A | 2/1996 | Seymour |
| 5,496,562 A | 3/1996 | Burgoyne |
| 5,658,548 A | 8/1997 | Padhye et al. |
| RE35,716 E | 1/1998 | Stapleton et al. |
| 5,756,126 A | 5/1998 | Burgoyne |
| 5,807,527 A | 9/1998 | Burgoyne |
| 5,811,061 A | 9/1998 | Martinson et al. |
| 5,863,801 A | 1/1999 | Southgate et al. |
| 5,922,591 A | 7/1999 | Anderson et al. |

(Continued)

FOREIGN PATENT DOCUMENTS

| | | |
|---|---|---|
| AU | 30256/84 B | 1/1985 |
| EP | 0130523 | 1/1985 |

(Continued)

OTHER PUBLICATIONS

Biggar et al., 1999, "Virus Levels in Untreated African Infants Infected with Human Immunodeficiency Virus Type 1," The Journal of Infectious Diseases, 180(6):1838-1843.

Brambilla et al., 2003, "Multicenter Evaluation of Use of Dried Blood and Plasma Spot Specimens in Quantitative Assays for Human Immunodeficiency Virus RNA: Measurement, Precision, and RNA Stability," American Society for Microbiology, 41(5):1888-1893.

Cassol et al., 1997, "Quantification of Human Immunodeficiency Virus Type 1 RNA from Dried Plasma Spots Collected on Filter Paper," Journal of Clinical Microbiology, 35(11):2795-2801.

(Continued)

*Primary Examiner* — Natalia Levkovich
(74) *Attorney, Agent, or Firm* — Sutherland Asbill & Brennan LLP

(57) ABSTRACT

The present invention provides methods for collecting, storing or transporting liquid suspension of biological specimens containing analytes of interest in a dry state. The dried biological specimens containing analytes of interest are reconstituted and released for subsequent analysis by compressing or centrifuging the matrix. Also provided are method of using kits for collecting, storing, transporting and recovering biological specimens containing analytes of interest.

26 Claims, 7 Drawing Sheets

(56) References Cited

U.S. PATENT DOCUMENTS

| | | | |
|---|---|---|---|
| 5,939,259 | A | 8/1999 | Harvey et al. |
| 5,972,386 | A | 10/1999 | Burgoyne |
| 5,976,572 | A | 11/1999 | Burgoyne |
| 6,004,579 | A | 12/1999 | Bathurst et al. |
| 6,054,277 | A | 4/2000 | Furcht et al. |
| 6,153,104 | A | 11/2000 | Robertson |
| 6,187,540 | B1 | 2/2001 | Staub et al. |
| 6,231,815 | B1 | 5/2001 | Bainczyk et al. |
| 6,258,531 | B1 | 7/2001 | Bienhaus et al. |
| 6,294,203 | B1 | 9/2001 | Burgoyne |
| 6,322,983 | B1 | 11/2001 | Burgoyne |
| 6,447,804 | B1 | 9/2002 | Burgoyne |
| 6,503,747 | B2 | 1/2003 | Kathariou et al. |
| 6,627,226 | B2 | 9/2003 | Burgoyne et al. |
| 6,645,717 | B1 | 11/2003 | Smith et al. |
| 6,881,543 | B2 | 4/2005 | Philpott et al. |
| 2001/0000149 | A1 | 4/2001 | Smith et al. |
| 2002/0187561 | A1 | 12/2002 | Wong et al. |
| 2004/0022666 | A1 | 2/2004 | Biddle et al. |

FOREIGN PATENT DOCUMENTS

| | | |
|---|---|---|
| EP | 0221308 | 5/1987 |
| EP | 0261955 | 3/1998 |
| EP | 1405599 A1 | 4/2004 |
| EP | 0849992 B1 | 8/2004 |
| EP | 1484111 A1 | 12/2004 |
| GB | 2358061 A | 7/2001 |
| GB | 2383955 A | 7/2003 |
| WO | 90/03959 | 4/1990 |
| WO | 91/07486 | 5/1991 |
| WO | 93/07292 | 4/1993 |
| WO | 93/19207 | 9/1993 |
| WO | 94/04078 A1 | 3/1994 |
| WO | 96/00348 | 1/1996 |
| WO | 96/11406 | 4/1996 |
| WO | 96/26935 | 9/1996 |
| WO | 96/39813 | 12/1996 |
| WO | 96/41810 | 12/1996 |
| WO | 00/51496 A1 | 9/2000 |
| WO | 00/53807 A1 | 9/2000 |
| WO | 02/40699 A2 | 5/2002 |
| WO | 02/072870 A2 | 9/2002 |
| WO | 03/020924 A2 | 3/2003 |
| WO | 03/044211 A2 | 5/2003 |
| WO | 2004/033470 A2 | 4/2004 |

OTHER PUBLICATIONS

Cassol et al., 1992, "Stability of Dried Blood Spot Specimens for Detection of Human Immunodeficiency Virus DNA by Polymerase Chain Reaction," Journal of Clinical Microbiology, 30(12):3039-3042.

Evengard et al., 1989, "Effect of heat on extracted HIV viral infectivity and antibody activity using the filter paper technique of blood sampling," Current Science, 3(9):591-595.

Fiscus et al., 1998, "Quantitation of Human Immunodeficiency Virus Type 1 RNA in Plasma by Using Blood Dried on Filter Paper," Journal of Clinical Microbiology, 36(1):258-260.

Gwinn et al., 1991, "Prevalence of HIV Infection in Childbearing Women in the United States," JAMA, 265(13):1704-1708.

Nyambi et al., 1994, "Detection of Human Immunodeficiency Virus Type 1 (HIV-1) in Heel Prick Blood on Filter Paper from Children Born to HIV-1-Seropositive Mothers," Journal of Clinical Microbiology, 32(11):2858-2860.

O'Shea et al., 1999, "AIDS," http://www.AIDSonline.com, 13(5):630-631.

Panteleeff et al., 1999, "Rapid Method for Screening Dried Blood Samples on Filter Paper for Human Immunodeficiency Virus Type 1 DNA," American Society for Microbiology, 37(2):350-353.

Solmone et al., 2002, "Simple and Reliable Method for Detection and Genotyping of Hepatitis C Virus RNA in Dried Blood Spots Stored at Room Temperature," American Society for Microbiology, 40(9):3512-3514.

International Preliminary Report on Patentability dated Oct. 11, 2006 for PCT/US05/005392 (5 pages).

METHODS FOR COLLECTION, STORAGE AND TRANSPORTATION OF BIOLOGICAL SPECIMENS

CROSS REFERENCES TO RELATED APPLICATIONS

This application is a continuation of U.S. application Ser. No. 12/482,907, filed on Jun. 11, 2009, which is a divisional of U.S. application Ser. No. 11/061,698, filed on Feb. 18, 2005, now U.S. Pat. No. 7,638,099, issued on Dec. 29, 2009, which claims the benefit of U.S. Provisional Application Ser. No. 60/561,037, filed on Apr. 9, 2004, all of which are hereby incorporated by reference in their entirety herein.

FIELD OF THE INVENTION

This invention relates generally to devices and methods for collection, storage and transportation of a liquid suspension of biological specimens containing analytes of interest in a dry state. The invention further provides methods for recovery of the biological specimens containing analytes of interest for subsequent research laboratory analysis and clinical trial testing.

BACKGROUND OF THE INVENTION

Biological specimens are often collected, transported and stored for analysis of the levels and concentrations of various analytes contained therewithin. Conventionally, liquid suspensions of biological specimens are stored in sealed airtight tubes under refrigeration. Liquid sample collection, handling, transportation and storage has many problems associated with it, for example: the cost of refrigeration (typically by dry ice) in remote collection centers; the risk of container breakage or leakage which causes loss of sample and the danger of infection; sample instability during shipment and storage; refusal of transport carriers to accept liquid biohazard shipments; and collection of adequate sample volume to ensure quantities compatible with laboratory methods of subsequent analyses. The costs of addressing the above problems are substantial.

Dried blood spot (DBS) and dried plasma spot (DPS) sampling on filter paper are alternative methods to the liquid sampling procedures, and have been used worldwide with some success. Since the 1980s, manufacturers such as Schleicher and Schuell Corp., Bio-Rad, Boehringer Mannheim Corp., and Whatman, Inc., have been producing filter papers for DBS and DPS sampling. In using these commercially available biological sampling filter paper systems, a blood or plasma spot is placed in one or more designated areas of the filter paper, allowed to dry, and then mailed along with a test request form to the laboratory. Commonly used filter papers are known to those of ordinary skill in the art, such as Whatman 3 MM, GF/CM30, GF/QA30, S&S 903, GB002, GB003, or GB004. Several categories of blotting materials for blood specimen collection are available, e.g., S&S 903 cellulose (wood or cotton derived) filter paper and Whatman glass fiber filter paper. However, certain disadvantages have been associated with these commercially available filter papers. Specifically, certain of these commercially available and commonly used materials lack characteristics which provide precision values and accuracy that are preferred for carrying out certain biological assays.

Genetic material can be extracted and isolated from DBSs in sufficient quantities for use in genetic analysis. For instance, DBS has been used for the detection of prenatal human immunodeficiency virus (HIV) infection by the polymerase chain reaction (PCR) (Cassol, et al., J. Clin Microbiol. 30 (12): 3039-42, 1992). DPS and DBS have also been used for HIV RNA detection and quantification (Cassol, et al., J. Clin. Microbiol. 35: 2795-2801, 1997; Fiscus, et al., J. Clin. Microbiol. 36: 258-60, 1998; O'Shea, et al., AIDS 13: 630-1, 1999; Biggar, et al., J. Infec. Dis. 180 1838-43, 1999; Brambilla, et al., J. Clin. Microbiol. 41(5): 1888-93, 2003); HIV DNA detection and quantification (Panteleefe, et al., J. Clin. Microbiol. 37: 350-3, 1999; Nyambi, et al., J. Clin. Microbiol. 32: 2858-60, 1994); and HIV antibody detection (Evengard, et al., AIDS 3: 591-5, 1989; Gwinn, et al., JAMA 265: 1704-08, 1991). HCV RNA detection and genotyping are also reported using DBS (Solmone et al., J. Clin. Microbio. 40 (9): 3512-14, 2002). Although these studies provide a good correlation with titers using DPS or DBS is obtained as compared with conventional liquid plasma samples, a loss of viral titers may occur after room temperature storage (Cassol, et al., J. Clin. Microbiol. 35: 2795-2801, 1997; Fiscus, et al., J. Clin. Microbiol. 36: 258-60, 1998). DBS and DPS samples are clearly less expensive and less hazardous to transport than liquid samples.

However, the procedure of analyte microextraction from DBS and DPS on filter paper suffers from a number of disadvantages. For example, microextraction of sufficient DNA or RNA from filter paper involves reconstitution in a liquid medium under certain vigorous procedures, e.g., vortex and centrifugation, that damages the genetic analytes of interest. Furthermore, the fibers and other components of the filters become dislodged into the reconstitution solution, and require further centrifugation separation and/or can impede the ability to isolate the genetic material, such as by blocking genetic material from adhering to a separation column. Such prior microextraction procedures require a high standard of technical assistance, and even then do not consistently provide results with a desired level of sensitivity and specificity.

Furthermore, the sample volume used for DBS and DPS on filter paper is limited, typically to 50 µl spots, and considerable difficulty in analyte detection can be encountered, particularly when the concentration of the desired analyte material is low in the sample. Also in the prior art, there is a lack of deliberate inhibition of enzymes and chemicals which degrade the analytes, such as genetic material contained therewithin. Even in the presence of a bacteriostatic agent there are conditions that permit enzymatic, nonenzymatic and autolytic breakdown of the genetic material. Furthermore, microextraction of genetic material from DBS or DPS on filter papers is considerably more difficult if absorption of high molecular weight DNA or RNA is required. Although the introduction of new material and transportation methods continuously improve the ways samples are handled, the quantity and quality of the sample available for subsequent analysis are still of great concern to researchers and clinicians alike.

Thus, there is a need for a safe, convenient and simple device for collection, storage and transportation of liquid suspension of biological specimens containing analytes of interest in a dry state, especially in large field studies and for application in settings where collection, centrifugation, storage and shipment can be difficult, as is often the case in developing countries. In addition, there is a need for improved recovery of the biological specimens for subsequent analysis that provides precision values and accuracy of detection of the analytes of interest contained therewithin.

SUMMARY OF THE INVENTION

This invention fulfills in part the need to provide a safe, convenient and simple device and method for collection, storage and transportation of liquid suspension of biological specimens containing analytes of interest. The invention also fulfills in part the need to recover biological specimens containing analytes of interest for subsequent analysis that provides more desirable sensitivity and specificity of detection. More particularly, the present invention provides a novel dried specimen technology and transport medium for the collection and transportation of liquid suspension of biological specimens in a dry state for use in research and site validated clinical testing.

The present invention provides a technology that allows for biological testing of air-dried bodily fluid samples without the need for refrigerated or frozen shipping and storage. The present invention also provides a technology that has the capability to significantly reduce the costs of shipping infectious materials worldwide, especially those associated with large clinical trials. Moreover, the present invention provides a technology that is applicable to and includes a wide range of esoteric and standard clinical testing.

The present invention describes a device for collecting, storing or transporting a biological specimen containing analytes of interest. More particularly, the device comprises a container defining an interior space having side walls, a bottom and a lid which may be opened. In one preferred embodiment, the invention provides a container having a threaded screw cap. The device further comprises a matrix inside the container. The matrix absorbs at least 0.1 ml of a liquid suspension of biological specimens, and is able to be compressed by at least 50% of the volume of the matrix to release a portion of the biological specimen. In certain embodiments, the device also has a desiccant inside the container in vaporous communication with the matrix to dry the liquid suspension.

In another preferred embodiment, the invention includes a dry solid matrix for storage of a liquid suspension of biological specimens which absorbs at least 0.5 ml of the liquid suspension. In yet another preferred embodiment, the matrix absorbs 1 ml of the liquid suspension of biological specimens.

According to other embodiments of the present invention, the matrix is compressible by at least 50% of the volume of the liquid saturated matrix to release a portion of the liquid suspension of biological specimen stored therewithin. In other embodiments, the matrix is compressed by at least 75% of the volume of the matrix to release a portion of the liquid suspension of biological specimen stored in the matrix. In preferred embodiments, the matrix is porous and three-dimensional in a variety of different shapes. Preferably, the shape of the matrix is a cylinder, cube, sphere, pyramid, cone or other shapes suitable for absorption and fitting inside a container. In one of the preferred embodiments, the matrix is in the shape of a cylinder about 20 mm in length and 8 mm in diameter.

The invention also provides that the matrix is made from an absorbent material. The absorbent material includes, but is not limited to, cellulose acetate fibers, wood or cotton derived cellulose, nitrocellulose, carboxymethylcellulose, hydrophilic polymers including polypropylene, polyester, polyamide, carbohydrate polymers, polytetrafluoroethylene, glass fiber, nylon, and combinations thereof.

The invention also provides that the device includes a matrix that is removable from the container. In preferred embodiments, the matrix is removably mounted in a holder on the lid of a container. In one of the preferred embodiments, the matrix is removably mounted in an extension of a screw cap that attaches to the threads of the container tube.

According to the invention, the analytes of interest include, but are not limited to, nucleic acids, proteins, carbohydrates, lipids, whole cells, cellular fragments, whole virus or viral fragments. In preferred embodiments, the analytes of interest are nucleic acids including either or both DNA and RNA molecules. According to the invention, the biological specimens include, but are not limited to, whole blood, plasma, urine, saliva, sputum, semen, vaginal lavage, bone marrow, cerebrospinal fluid, other physiological or pathological body liquids, or any of the combinations thereof. Preferably, the biological specimen is human body fluid, more preferably, the biological specimen is the whole blood, most preferably, the analytes are nucleic acids, including either or both DNA and RNA molecules. In one of the preferred embodiments, the analytes of interest are nucleic acids and the biological specimens comprise at least 500 ng to 1 µg either or both DNA or RNA molecules. In yet another preferred embodiment, the biological specimen is contained in liquid suspension. According to the present invention, the liquid suspension includes but is not limited to cell suspension, liquid extracts, tissue homogenates, media from DNA or RNA synthesis, saline or any combinations thereof.

The invention further provides that the device includes a desiccant inside the container in vaporous communication with the matrix to keep the liquid suspension dry. In preferred embodiments, the desiccant is montmorillonite clay, lithium chloride, activated alumina, alkali alumino-silicate, DQ11 Briquettes, silica gel, molecular sieve, calcium sulfate, or calcium oxide. In preferred embodiments, the desiccant indicates its moisture content by colorimetric means.

The invention further provides a method for collecting, storing or transporting a liquid suspension of a biological specimen containing analytes of interest in the device provided by the present invention. The method comprises the following steps: (a) applying a liquid suspension of biological specimen containing analytes of interest to the matrix of the device, and (b) sealing the lid on the device for collection, storage or transportation. In preferred embodiments, the method comprises an intermediate step of applying a stabilizing liquid to the matrix, wherein the stabilizing liquid comprises compositions for the protection of analytes of interest from chemical damage and degradation. The protecting compositions include, but are not limited to, a weak base, a chelating agent, a free radical trap, a protein denaturing agent and a nuclease inhibitor.

The present invention further provides a method for recovering a biological specimen containing analytes of interest from the matrix in the device provided by the present invention. In preferred embodiments, the method comprises the following steps: (a) applying reconstitution buffer to the matrix in the device to rehydrate the bound biological specimen, and (b) compressing the matrix in the device to release a portion of the biological specimen. According to the present invention, the reconstitution buffer comprises 1× phosphate buffered saline (PBS) or nuclease-free water optionally comprising sodium azide or other antimicrobial agent. The reconstitution buffer may also include any number or combinations of available biological preservatives or blood anticoagulants including but not limited to ethylenediaminetetraacetic acid (EDTA), sodium citrate, and heparin. In one of the preferred embodiments, the method further comprises a step of removing the matrix from the container prior to compressing the matrix. In yet another preferred embodiment, the compression of the matrix is achieved by placing the matrix in a syringe barrel and applying force to a plunger against the matrix. According to the present invention, the matrix in the device is capable of compressing by at least 50% of the volume of the matrix, preferably at least 75%, 80%, 85% or 90% of the volume of the matrix to release a portion of the biological specimen suspended in the matrix.

The present invention further provides a kit for collecting, storing or transporting a liquid suspension of a biological specimen containing analytes of interest. In preferred embodiments, the kit includes the device provided by the present invention and instructions for collection and storage of the specimen. The kit can further comprise a stabilizing solution to inhibit degradation of the analytes. The kit can further comprise a reconstitution buffer, a compression device and further instructions for recovery of the biological specimen. In one of the preferred embodiments, the compression device is a syringe barrel with a plunger, wherein the compression of the matrix of the device is achieved by placing the matrix in the syringe barrel and applying force to the plunger, and wherein at least 50% to 90% or greater of the volume of the matrix is compressed to release a portion of the bound biological specimen.

The present invention further provides subsequent analysis using the recovered biological specimen containing analytes of interest. In preferred embodiments, the analytes of interest are nucleic acids including either or both DNA and RNA molecules that are detected or analyzed using analytical and diagnostic methods known in the art.

DETAILED DESCRIPTION OF THE INVENTION

Figure 1A:
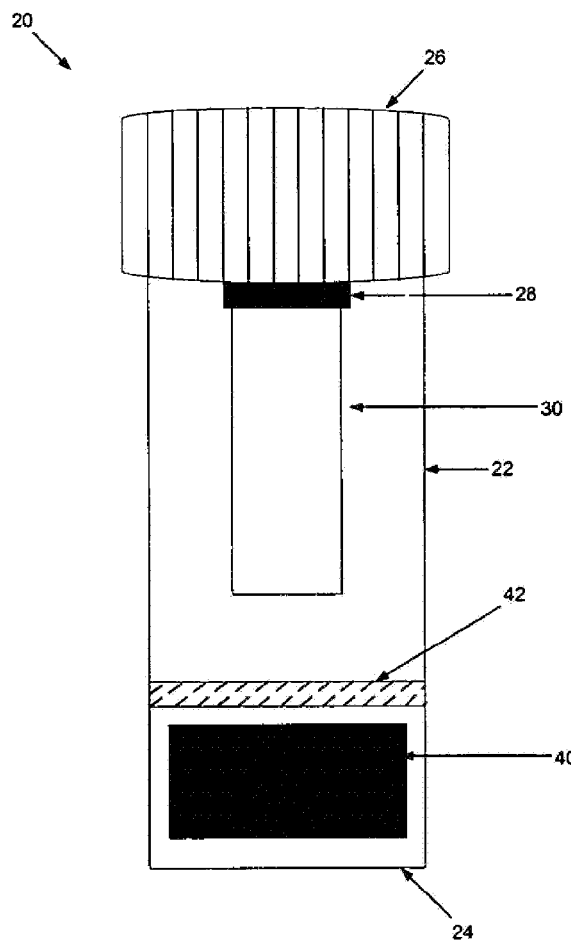
FIG. 1A is a perspective view of an assembled device according to one embodiment of the present invention.

The present invention may be understood more readily by reference to the following detailed description of the preferred embodiments of the invention and the Examples included herein. However, before the present devices, materials, and methods are disclosed and described, it is to be understood that this invention is not limited to specific embodiments of the devices, materials and methods, as such may, of course, vary, and the numerous modifications and variations therein will be apparent to those skilled in the art. It is also to be understood that the terminology used herein is for the purpose of describing specific embodiments only and is not intended to be limiting.

The present invention provides a device and method for collection, storage and transportation of a liquid suspension of a biological specimen containing an analyte of interest. More particularly, the present invention provides a device and method for collection, storage and transportation of a liquid suspension containing a biological specimen in a dry state that is convenient and simple to use. As used herein, the terms "a" or "an" mean one or more than one depending upon the context in which they are used. For example, "an analyte" in a sample refers to a particular type of analyte of interest (e.g. HIV DNA), of which there may be numerous copies within the sample. Where a sample is referred to as containing an analyte, it is understood that the sample may contain many other types of analytes of interest also.

As used herein, the phrase "collection, storage and transportation" refers to the preservation of liquid suspension of biological specimen containing analytes of interest in a form suitable for subsequent analysis. The time period for which biological specimen may be preserved according to the present invention may be as short as the time necessary to transfer a sample of biological specimen from a collection source to the place where subsequent analysis is to be performed. Therefore, the invention provides that such preservation can occur for a period of several minutes, hours, days, months or greater. The temperature conditions under which a biological specimen may be stored in the device provided by the present invention are not limited. Typically, samples are shipped and/or stored at ambient or room temperature, for example, from about 15° C. to about 40° C., preferably about 15° C. to 25° C. In another embodiment the samples may be stored in a cool environment. For example, in short-term storage, the samples can be refrigerated at about 2° C. to about 10° C. In yet another example, the samples may be refrigerated at about 4° C. to about 8° C. In another example, in long-term storage, the samples can be frozen at about −80° C. to about −10° C. In yet another example, the samples can be frozen from about −60° C. to about −20° C. In addition, the device may preferably but not necessarily be stored in dry or desiccated conditions or under an inert atmosphere.

In preferred embodiments, the present invention provides a device comprising a container defining an interior space having side walls, a bottom and a lid which may be opened. In one preferred embodiment, the invention provides a container having a threaded screw cap. In other embodiments, the lid can remain attached to the container such as a flip-top fashion. In another embodiment, the lid may also be cork-like. The lid preferably provides an air-tight seal when the container is closed. The shape of the container is not limited, but can be cylindrical, rectangular, or tubular for example. Materials for construction of the container are not limited, but can be plastic, metal foil, laminate comprising metal foil, metallized film, glass, silicon oxide coated films, aluminum oxide coated films, liquid crystal polymer layers, and layers of nano-composites, metal or metal alloys, acrylic, and amorphous carbon for example.

In another embodiment, the lid may be sealed to the container by heating. Suitable seals include, but are not limited to, lap seals, fin seals, butt seals, and the like, and the seals can be made by any of the suitable means known to those skilled in the art such as heating sealing, or the application of cold or hot melt adhesives, a heated bar, hot air, infrared radiation, ultrasonic sealing, radio frequency sealing, laser sealing, and the like.

The device also comprises a matrix inside the container. The matrix has an ability to absorb a liquid suspension readily and quickly, as well as to release the biological specimen containing analytes of interest efficiently and precisely. In preferred embodiments, the matrix can absorb at least 0.1 ml, 0.2 ml, 0.3 ml, 0.4 ml, 0.5 ml, 0.6 ml, 0.7 ml, 0.8 ml, or 0.9 ml, or preferably 1.0 ml, or greater, sample of a liquid suspension of a biological specimen containing an analyte of interest. The term "absorb" and "adsorb" are used interchangeably, and means that the liquid suspension is incorporated into or onto the matrix in such a way as to not be readily removed from the matrix unless subjected to conditions which are intentionally or inadvertently performed to remove the absorbed liquid suspension of biological specimen or the reconstituted biological sample from the matrix.

The volume of the matrix may or may not expand upon absorption of the liquid suspension, and may or may not contract upon drying. However, a liquid saturated matrix can be compressed by at least about 20%, 30%, 40%, 50%, 60%, 70%, 75%, 80%, or 90% of its saturated volume. Volumetric compression is one convenient technique for release of the reconstituted biological specimen, however, any other means, such as centrifugation, can alternatively be employed to release the biological specimen from the matrix.

Therefore, as used herein, the term "compress," "compressable," "compression," and other derivatives of the word "compress" means that the volume of the saturated matrix is reduced as compared to the original volume of the saturated matrix while a force or a pressure is applied to the matrix. As used herein, the term "a portion of the biological specimen" means at least some of the biological specimen contained in the liquid suspension is released from the matrix. In one preferred embodiment, the matrix is compressed until the maximum volume of the reconstituted biological specimen is released from the matrix.

In preferred embodiments, the matrix is three-dimensional in a shape such as cylinder, cube, sphere, pyramid or cone. In one of the preferred embodiments, the matrix is in the shape of a cylinder about 20 mm in length and 8 mm in diameter. However, the matrix can be widened, lengthened, or shortened to achieve any needed volume capacity. In yet another preferred embodiment, the matrix is removable from a container. As used herein, the term "removable" means that the matrix can be detached or separated from the container. In one of the preferred embodiments, the matrix is removably mounted in a holder on the lid of a container. In yet another preferred embodiment, the matrix is removably mounted to a lid extension of the transportation or storage container. In other embodiments, the matrix can be mounted in the container, and compressed therein to release reconstituted biological suspension through a port for example.

The matrix of the present invention includes any absorbent material to which the liquid suspension of biological specimen containing analytes of interest will absorb and which does not inhibit storage or subsequent analysis of the analytes of interest applied thereto. The material of the matrix itself preferably has no or minimal effect on the measurement or detection of the analytes of interest. In preferred embodiments, the matrix comprises an absorbent material that is of a porous nature to provide entrainment of the liquid suspension in the matrix. As used herein, the term "entrain" and derivatives thereof means that during storage the liquid suspension is bound to the matrix without substantial reliance on ionic, covalent or van der waals interactions. A matrix suitable for this purpose includes, but is not limited to, a matrix that is composed of cellulose acetate fibers, wood or cotton derived cellulose, nitrocellulose, carboxymethylcellulose, hydrophilic polymers including polyproplylene, polyester, polyamide, carbohydrate polymers, polytetrafluoroethylene, glass fiber, nylon, and combinations thereof.

As used herein, the term "liquid suspension" refers to any liquid medium and mixture containing biological specimens. This includes, for example, water, saline; cell suspensions of humans, animals and plants; extracts or suspensions of bacteria, fungi, plasmids, viruses; extracts or suspensions of parasites including helminthes, protozoas, spirochetes; liquid extracts or homogenates of human or animal body tissues, e.g., bone, liver, kidney, brain; media from DNA or RNA synthesis; mixtures of chemically or biochemically synthesized DNA or RNA, and any other sources in which any biological specimen is or can be in a liquid medium.

As used herein, the term "biological specimen" refers to samples, either in liquid or solid form, having dissolved, suspended, mixed or otherwise contained therein, any analytes of interest, for example, genetic material. As used herein, the term "genetic material" refers to nucleic acids that include either or both deoxyribonucleic acid (DNA) or ribonucleic acid (RNA). The term "biological specimen" also refers to whole blood, plasma, serum, lymph, synovial fluid, bone marrow, cerebrospinal cord fluid, semen, saliva, urine, feces, sputum, vaginal lavage, skin scrapings, hair root cells, or the like of humans or animals, physiological and pathological body liquids, such as secretions, excretions, exudates and transudates; any cells or cell components of humans, animals, plants, bacterials, fungi, plasmids, viruses, parasites, or the like that contain analytes of interest, and any combination thereof.

As used herein, the term "analytes of interest" refers to any micro- or macro-molecules in the biological specimen that are interested to be detected or analyzed. These include, for example, nucleic acids, polynucleotides, oligonucleotides, proteins, polypeptides, oligopeptides, enzymes, amino acids, receptors, carbohydrates, lipids, cells, any intra- or extracellular molecules and fragments, virus, viral molecules and fragments, or the like. In one of the preferred embodiments, the analytes of interest are nucleic acids including either or both DNA or RNA. As used herein, the term "nucleic acids" or "polynucleotide" refers to RNA or DNA that is linear or branched, single or double stranded, a hybrid, or a fragment thereof. The term also encompasses RNA/DNA hybrids. The term also encompasses coding regions as well as upstream or downstream noncoding regions. In addition, polynucleotides containing less common bases, such as inosine, 5-methylcytosine, 6-methyladenine, hypoxanthine, and other are also encompassed. Other modifications, such as modification to the phosphodiester backbone, or the 2'-hydroxy in the ribose sugar group of the RNA are also included. The nucleic acids/polynucleotides may be produced by any means, including genomic preparations, cDNA preparations, in vitro synthesis, RT-PCR, and in vitro or in vivo transcription. In one preferred embodiment, the nucleic acids are either or both viral DNA or RNA, for example, DNA or RNA from human immunodeficiency virus (HIV), hepatitis B virus (HBV), hepatitis C virus (HCV), or any other human or animal viral pathogen.

In preferred embodiments, the device provided by the present invention also includes a desiccant, either a natural or synthetic desiccant, inside the container to create and maintain dry conditions within the container. Preferably, the desiccant is in vaporous communication with the matrix in the device having a dye indicator reactive with moisture whereby the desiccant changes to a bright color when exposed to humidity or moisture. In one of the preferred embodiments, the desiccant is in vaporous communication with the matrix so that an air permeable barrier is formed in-between the desiccant and the matrix inside the container. The desiccant used in the device is commonly known in the art, including but not limited to montmorillonite clay, lithium chloride, activated alumina, alkali alumino-silicate, DQ11 Briquettes, silica gel, molecular sieve, calcium sulfate, and calcium oxide. The desiccant can be provided with a colorimetric indicator of water content.

The matrix of the invention may optionally include a composition absorbed to the matrix wherein the composition protects against degradation of the analytes of interest contained in the biological specimens. As used herein, the term "protects against degradation of the analytes of interest" means that a matrix in the device of the invention maintains the stored analytes of interest contained in the biological specimens in a substantially nondegraded form, providing that the analytes of interest are suitable for many different types of subsequent analytical procedures. Protection against degradation may include protection against substantial damaging of analytes of interest caused by chemical or biological agents including action of bacteria, free radicals, nucleases, ultraviolet radiation, oxidizing agent, alkylating agents, or acidic agents (e.g., pollutants in the atmosphere). Preferably, the composition absorbed on the matrix of the invention may include one or more of a weak base, a chelating agent, a protein denaturing agent such as a detergent or surfactant, a nuclease inhibitor, and a free radical trap. In the case where the stored analyte of interest is RNA, particularly unstable RNA, the composition may include RNase inhibitors and inactivators, genetic probes, complementary DNA or RNA (or functionally equivalent compounds), proteins and organic moieties that stabilise RNA or prevent its degradation.

Another composition which protects against degradation which may be optionally used is an oxygen scavenger element. As used herein, the term "oxygen scavenging element" refers to is a substance that consumes, depletes or reduces the amount of oxygen from a given environment without negatively affecting the samples of interests. Suitable oxygen scavenging elements are well-known to those skilled in the art. Non-limiting examples of oxygen scavenging elements include but are not limited to compositions comprising metal particulates reactive with oxygen such as transition metals selected from the first, second or third transition series of the periodic table of the elements, and include manganese II or III, iron II or III, cobalt II or III, nickel II or III, copper I or II, rhodium II, III or IV, and ruthenium. The transition metal is preferably iron, nickel or copper. An example of an iron oxygen scavenging element is D500 from Multisorb. Other commercially available oxygen scavengers may also be purchased from companies such as Mitsubishi, Dow, or the like. Other examples of oxygen scavenging element may be enzymes which consumes, depletes or reduces the amount of oxygen from the given environment without negatively affecting the samples of interests.

In another embodiment, the container may optionally comprise a modified atmosphere such as nitrogen or argon through well known gas purging process prior to sealing, shipping, or storing. The term "modified atmosphere" refers to any replacing or altering normal atmospheric gas compositions with at least one inert gas or gas which does not degrade the sample of interests.

As used herein, a "weak base" suitable for the composition of the invention may be a Lewis base which has a pH of about 6 to 10, preferably about pH 8 to 9.5. The weak base suitable for the composition of the invention may, in conjunction with other components of the composition, provide a composition pH of 6 to 10, preferably, about pH 8.0 to 9.5. Suitable weak bases according to the invention include organic and inorganic bases. Suitable inorganic weak bases include, for example, an alkali metal carbonate, bicarbonate, phosphate or borate (e.g., sodium, lithium, or potassium carbonate). Suitable organic weak bases include, for example, tris-hydroxymethyl amino methane (Tris), ethanolamine, triethanolamine and glycine and alkaline salts of organic acids (e.g., trisodium citrate). A preferred organic weak base is a weak monovalent organic base, for example, Tris. The weak base may be either a free base or a salt, for example, a carbonate salt. It is believed that the weak base may provide a variety of functions, such as protecting the analytes of interest from degradation, providing a buffer system, ensuring proper action of the chelating agent in binding metal ions, and preventing the action of acid nucleases which may not be completely dependent on divalent metal ions for functioning.

As used herein, a "chelating agent" is any compound capable of complexing multivalent ions including Group II and Group III multivalent metal ions and transition metal ions (eg., Cu, Fe, Zn, Mn, etc). Preferably, the chelating agent is ethylene diamine tetraacetic acid (EDTA), citrate or oxalate. It is believed that one function of the chelating agent is to bind multivalent ions which if present with the stored biological specimen may cause damage to the analytes of interest, especially to nucleic acids. Ions which may be chelated by the chelating agent include multivalent active metal ions, for example, magnesium and calcium, and transition metal ions, for example, iron. Both calcium and magnesium are known to promote nucleic acid degradation by acting as co-factors for enzymes which may destroy nucleic acids (e.g., most known nucleases). In addition, transition metal ions, such as iron, may readily undergo oxidation and reduction and damage nucleic acids by the production of free radicals or by direct oxidation.

The composition can further include a protein denaturing agent if the analytes of interest are nucleic acids. As used herein, a "protein denaturing agent" functions to denature non-nucleic acids compounds, for example, nucleases. If the protein denaturing agent is a detergent or a surfactant, the surfactant may also act as a wetting agent to facilitate the uptake of a sample by the dry solid matrix. The terms "surfactant" and "detergent" are synonymous and may be used interchangeably throughout the specification. Any agent which denatures proteins without substantially affecting the nucleic acids of interest may be suitable for the invention. Preferred protein denaturing agents include detergents. As used herein "detergents" include ionic detergents, preferably anionic detergents. A preferred anionic detergent suitable for the invention may have a hydrocarbon moiety, such as an aliphatic or aromatic moiety, and one or more anionic groups. Particularly preferred anionic detergents include sodium dodecyl sulphate (SDS) and sodium lauryl sarcosinate (SLS). The ionic detergent causes inactivation of a microorganism which has protein or lipid in its outer membranes or capsids, for example, fungi, bacteria or viruses. This includes microorganisms which may be pathogenic to humans or which may cause degradation of nucleic acids. It is believed that inactivation of a microorganism by a detergent is a result of destruction of the secondary structure of the organisms external proteins, internal proteins, protein containing membranes, or any other protein necessary for viability. However, the detergent may not inactivate some forms of organisms, for example, highly resistant bacterial spores and extremely stable enteric virions.

The composition of the invention may optionally include a free radical trap. As used herein, a "free radical trap" is a compound which is sufficiently reactive to be preferred, over a DNA molecule or a component thereof, as a reactant with a free radical, and which is sufficiently stable not to generate damaging free radicals itself. Examples of a suitable free radical trap include: uric acid or a urate salt, mannitol, benzoate (Na, K, Li or tris salt), 1-3 dimethyl uric acid, guanidine, guanine, thymine, adenine, cytosine, in N-acetyl-histidine, histidine, deferoxamine, dimethyl sulfoxide, 5'5' dimethylpyrroline-N-oxide, thiocyanate salt and thiourea. Preferred free radical traps include mannitol, thiocyanate salts, uric acid or a urate salt. It is believed that the longer the period of time for which the nucleic acid is to be stored the more likely that a free radical trap may be advantageously included in the composition sorbed to the solid matrix. Even if the nucleic acid is only to be stored for a matter of minutes, a free radical trap may still be incorporated into the composition. It is believed that one function of the free radical trap may be to trap nucleic acid damaging free radicals. For example, when the free radical trap used is uric acid or urate salt it may be converted to allantoin which may also act as a free radical trap that preferentially accepts free radicals that would otherwise damage nucleotide bases, for example, guanine. Preferably, the free radical trap reacts with free radicals regardless of source (including free radicals present in the air). Free radicals may be generated through oxidation or reduction of iron in biological specimen, such as blood. Typically, free radicals are believed to be generated by spontaneous oxidation of the groups which are present, for example, in denatured serum protein of blood. Free radicals may also be generated by radiation such as UV light, x-rays and high-energy particles. In addition, free radical traps which are also a weak acid, e.g. uric acid, may also function as a component of the buffering system provided by the weak base discussed above. Also, the free radical trap may enhance removal of a stored sample of nucleic acids if in situ processing is not desired.

Figure 1B:
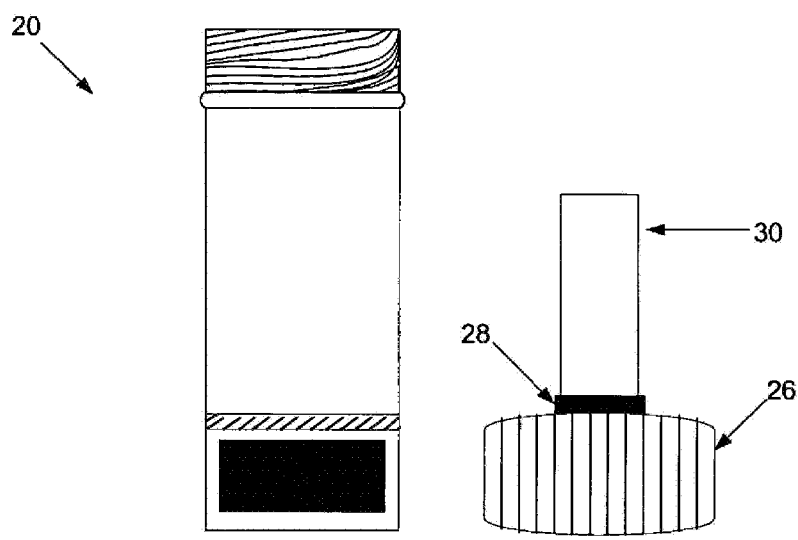
FIG. 1B is a perspective view of a disassembled device according to one embodiment of the present invention ready for sample addition.
Figure 2:
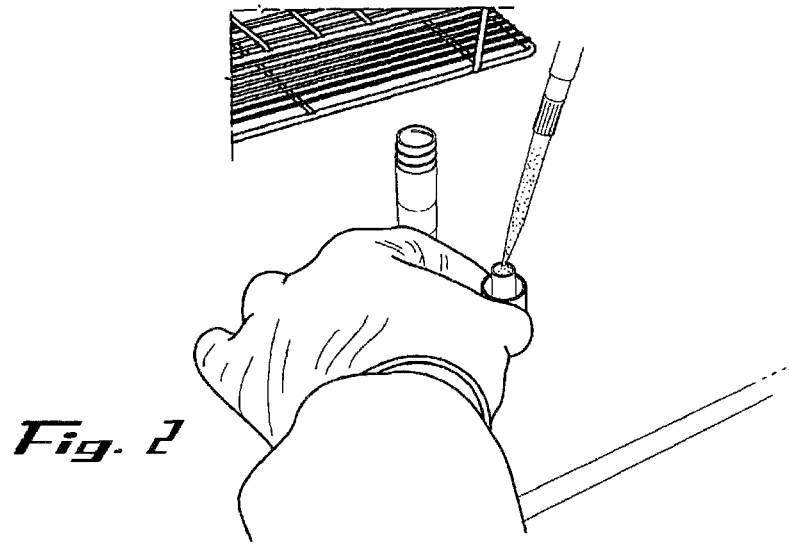
FIG. 2 illustrates addition of sample to the matrix of a device according to one embodiment of the present invention

Referring to FIGS. 1A & 1B, an exemplary transportation or storage device of the invention is shown for collecting, storing and transporting liquid suspension of biological specimen containing analytes of interest is shown. The container 20 is cylindrical and has side walls 22, a bottom 24 and an openable lid 26, which sealingly engages the container 20 opening. The lid 26 has an extension 28 that holds a removable matrix 30 inside the container 20. The matrix 30 is a cylinder capable of absorbing 1 ml of a liquid suspension of a biological specimen and compress by at least 50% of the volume of the saturated matrix to release a portion of the biological specimen. Accordingly, a desiccant 40 is also placed inside the container 20, separated with the matrix 30 by an optional air permeable barrier 42, for in vaporous communication with the matrix 30 to control humidity or moisture therein.

The present invention further provides a method for collecting, storing or transporting a liquid suspension of biological specimen containing analytes of interest. The method includes: a) applying the liquid suspension of biological specimen to the matrix in the device, and b) sealing the lid/cap on the device after the liquid suspension applied thereon is dry. In preferred embodiments, the liquid suspension is air-dried at room temperature. Other commonly available drying methods, such as vacuum dry, low heat dry, low pressure dry, and fan dry, may also be used.

Figure 3:
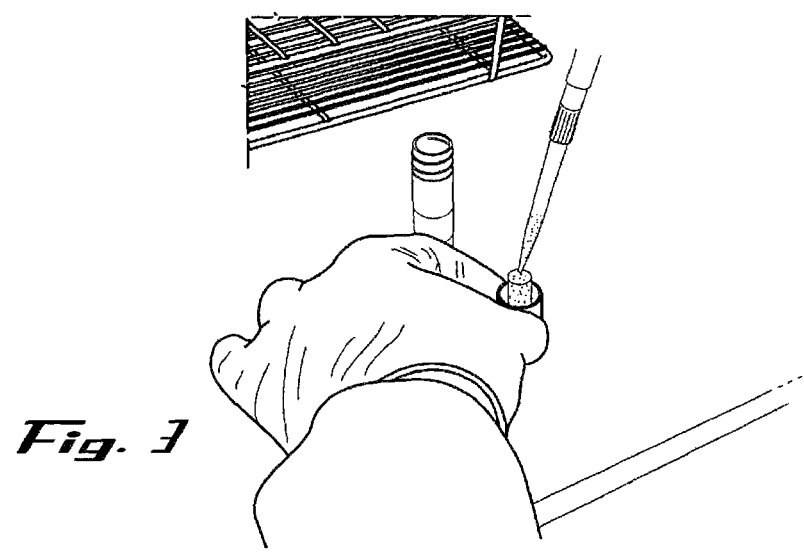
FIG. 3 illustrates completed addition of sample to the saturated matrix of a device according to one embodiment of the present invention.

Referring to FIG. 1B, the lid 26 of the container 20 has a lid extension 28 holding a removable matrix 30 which is disassembled. A liquid suspension of any biological specimen containing analytes of interest is added on the top of the matrix 30 and is allowed to fully absorb into the matrix 30 (See FIG. 3). The lid 26 with the matrix 30 having bound biological specimen thereon is allowed to air-dry, and then reassembled with the container 20 for storage or transportation at ambient temperature.

The method of the present invention further optionally includes an intermediate step of applying a stabilizing composition to the matrix to protect the analytes of interest against degradation. Depending upon the analytes of interest, the stabilizing composition, as discussed above, may include but is not limit to one or more of a weak base, a chelating agent, a protein denaturing agent such as a detergent or surfactant, a nuclease inhibitor, and a free radical trap. Particularly for protection of unstable RNA, the stabilizing composition may include RNase inhibitors and inactivators, genetic probes, complementary DNA or RNA (or functionally equivalent compounds), proteins and organic moieties that stabilise RNA or prevent its degradation.

The present invention further provides a method for recovering from the matrix in the device the biological specimen containing analytes of interest. In preferred embodiments, the method includes the following steps: a) applying reconstitution buffer to the matrix to rehydrate the bound biological specimen containing analytes of interest, and b) compressing the matrix to release a portion of the biological specimen. According to the present invention, the reconstitution buffer includes the components of 1× phosphate buffered saline (PBS) or nuclease-free water optionally with the addition of sodium azide or other antimicrobial agent. The reconstitution buffer may also include any number or combinations of available biological preservatives or blood anticoagulants including but not limited to ethylenediaminetetraacetic acid (EDTA), sodium citrate, and heparin. PBS or nuclease-free water serves as the sterile and neutral medium for the rehydration, resuspension, and recovery of the analyte(s) of interest from the matrix. When included, antimicrobial agents such as sodium azide prevent microbial growth and subsequent contamination with RNases. When included, biological preservatives such as EDTA, sodium citrate, and heparin serve as anticoagulants and or chelating agents.

Figure 4:
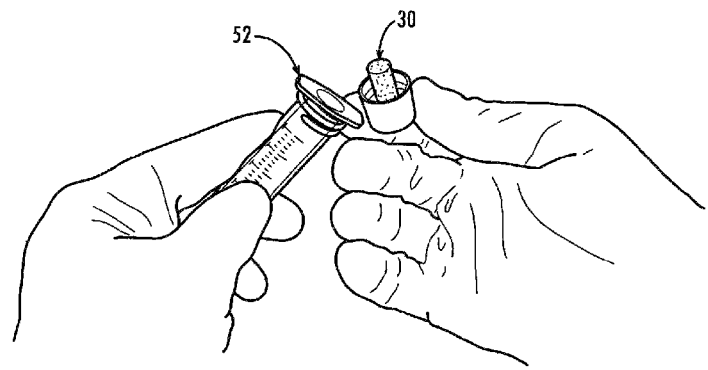
FIG. 4 is a perspective view of preparing to transfer the matrix of a device according to one embodiment of the present invention into an empty syringe barrel.
Figure 5:
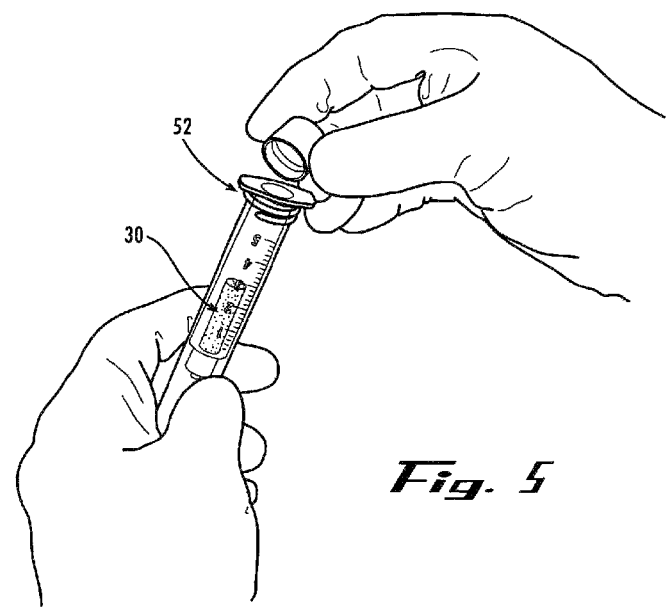
FIG. 5 is a perspective view of completed delivery of the matrix into the syringe barrel.

In the embodiments shown in FIGS. 4-7, the biological sample is prepared for analysis. FIG. 4. is a perspective view of preparing to transfer the matrix 30 of the device an the empty syringe barrel 52. FIG. 5 is a perspective view of completed delivery of the matrix 30 into the syringe barrel 52.

Figure 6:
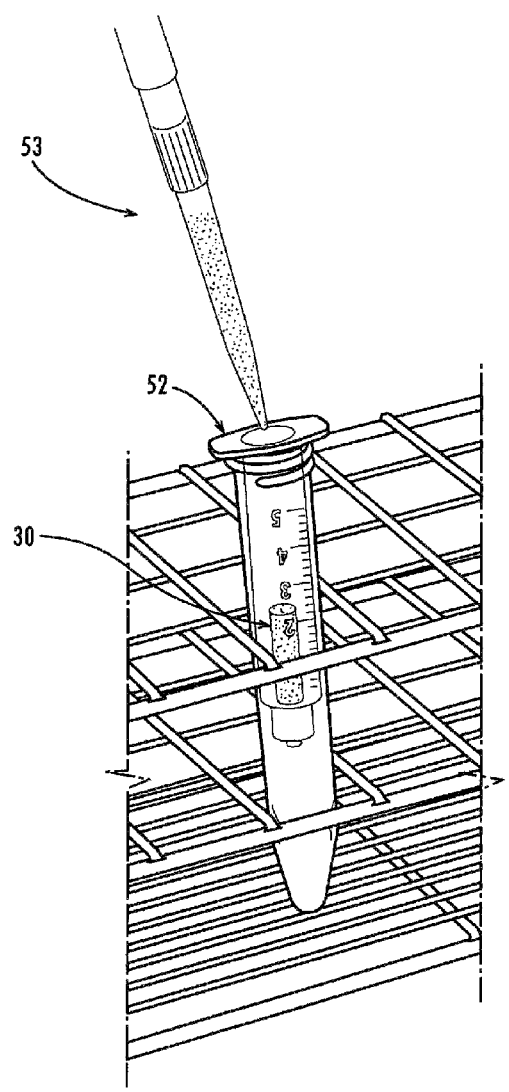
FIG. 6 illustrates rehydration of the matrix by a pipette tip gently placed on the top of the matrix and slowly dispensing reconstitution buffer.
Figure 7A:
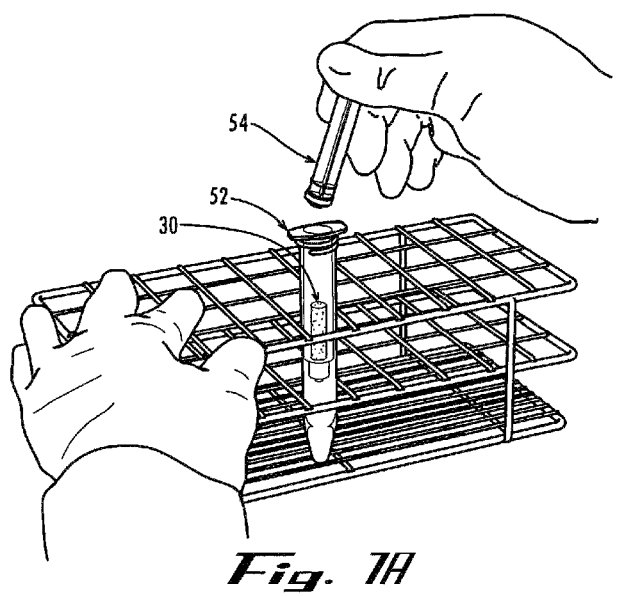
FIG. 7A illustrates insertion of the plunger into the syringe barrel.
Figure 7B:
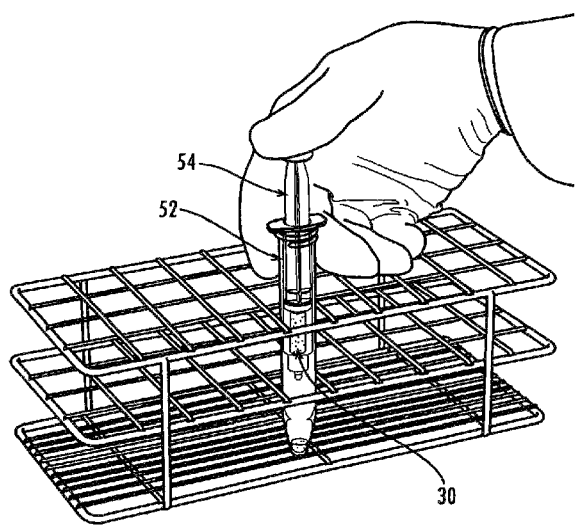
FIG. 7B illustrates application of pressure to the syringe plunger.
Figure 7C:
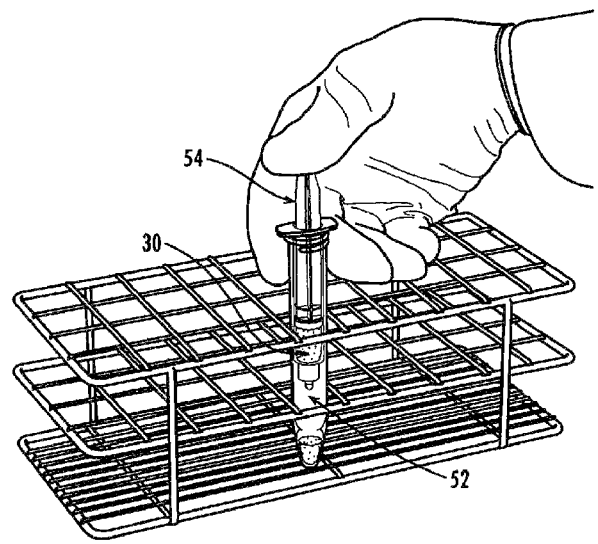
FIG. 7C illustrates compression of the matrix plug.
Figure 7D:
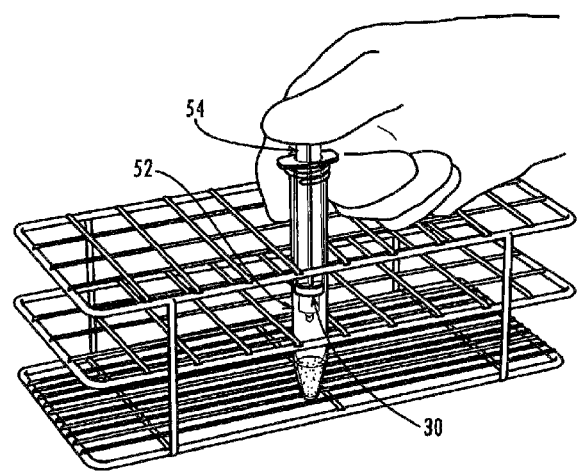
FIG. 7D illustrates completion of sample recovery.

FIG. 6 illustrates rehydration of the matrix 30 by a pipette tip 53 gently placed on the top of the matrix 30 and slowly dispensing reconstitution buffer. FIG. 7A illustrates insertion of the plunger 54 into the syringe barrel 54. FIG. 7B illustrates application of pressure to the syringe plunger 42. FIG. 7C illustrates compression of the matrix 30. FIG. 7D illustrates completion of sample recovery from the matrix 30.

In one of the preferred embodiments, the analytes of interest are nucleic acids including either or both DNA or RNA molecules. Preferably, the liquid suspension of biological specimen contains at least about 500 ng isolated DNA or RNA molecules, more preferably at least about 1 µg DNA or RNA molecules. As used herein, the term "isolated," "isolation," and other derivatives of the word "isolate" means that the DNA or RNA molecules are substantially free from some of the other cellular material with which it is naturally associated, or culture medium when produced by recombinant techniques, or chemical precursors or other chemicals when chemically synthesized.

The present invention further provides that the analytes of interest contained in the biological specimen recovered from the matrix of the device into the reconstitution buffer are subject to subsequent analysis. As used herein, the term "subsequent analysis" includes any analysis which may be performed on recovered biological specimens stored in reconstitution buffer. Alternatively, the analytes of interest contained in the biological specimen may be isolated, purified or extracted prior to analysis using methods known in the art. The analytes of interest may be subjected to chemical, biochemical or biological analysis. In one of the preferred embodiments, the analytes of interest are nucleic acids including either or both DNA or RNA molecules that can be detected or analyzed with or without prior extraction, purification or isolation. DNA or RNA extraction, purification or isolation, if necessary, is performed based on methods known in the art. Examples of subsequent analysis include polymerase chain reaction (PCR), ligase chain reaction (LCR), reverse transcriptase initiated PCR, DNA or RNA hybridization techniques including restriction fragment length polymorphism (RFLP), viral DNA or RNA detection and quantification, viral load tests, DNA or RNA genotyping, etc. "Subsequent analysis" also includes other techniques using genetic probes, genomic sequencing, enzymatic assays, affinity labeling, methods of detection using labels or antibodies and other similar methods.

The present invention also provides a kit for collecting, storing and transporting a liquid suspension of biological specimen containing analytes of interest. The kit of the present invention provides a device disclosed herein including one or more containers, one or more matrixes, and desiccant and instructions for the use thereof to collect biological specimens. The kit may optionally include a stabilising solution. Kits of the present invention can further include a reconstitution buffer, a compression device and further protocols for rehydration and recovery of the biological specimen. The container of the kit may be any container suitable for use during application of a liquid suspension of biological specimen containing analytes of interest to the matrix or during application and one or more phases of subsequent processing of a sample of the biological specimen. Therefore, a kit may be used to apply a liquid suspension to the matrix where the matrix is removed from the kit container for processing in a different container. Alternatively, a liquid suspension of biological specimen may be applied, stored, transported and further processed all in the same kit container.

The kit may also include one or more of any of the matrix disclosed herein. This includes one or more matrix with or without compositions for protection of analytes of interest contained in the biological specimen. One aspect of the kit of the present invention is that the reconstituted biological specimen containing analytes of interest is released by compressing the matrix. This procedure avoids vortexing and centrifuging the sample, providing decreased chance of sample damage, human labor costs and matrix contamination of the sample. A compression device of the kit of the present invention may be any device that is used to provide a force or pressure on the matrix to compress it. In one of the preferred embodiments, the compression device is a syringe, wherein the matrix is placed in the syringe barrel and the force or pressure is applied to the plunger of the syringe to compress the matrix to release the reconstituted biological specimen.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

One (1.0) ml Sample Preparation and Device Recovery Kit

Kit Components:
This example provides a kit for the preparation, transportation, and recovery of thirty-six (36) dry biological specimens from bodily fluids or tissue. Materials and reagents for the preparation and recovery of thirty-six (36) one (1.0) ml samples for dried ambient transportation include the following:

| Component | Quantity |
|---|---|
| Device Kit containers (tubes) | 36 each |
| Reconstitution Buffer | 3 × 13 ml |
| Disposable 3 ml Syringes | 36 each |
| 15 ml Conical Centrifuge Tubes | 36 each |

Storage and Handling:
Upon receipt, all kit components are stored dry at room temperature (15-25° C.). Only use device container tubes when the indicating desiccant is blue in color. The device kit container tubes should not be if the indicating desiccant appears white or pink in color. Materials, such as 1000 μl pipette, 1000 μl sterile DNase-free, RNase-free pipette tips with aerosol barrier, rack for holding 15 ml conical tubes, safety glasses, laboratory coat, powder-free disposable gloves and biohazard waste container, are also required but are not provided by the kit.

Safety Precautions:
Disposable powder-free gloves are used to handle all materials as though capable of transmitting infectious agents. Utilise good laboratory practices and universal precautions relating to the prevention of transmission of blood borne pathogens (See Centers for Disease Control. Update: Universal precautions for prevention of transmission of human immunodeficiency virus, hepatitis B virus and other blood borne pathogens in healthcare settings. MMWR, 1988; 37:377-82, 387-8; National Committee for Clinical Laborator Standards. Protection of laboratory workers from infectious disease transmitted by blood, body fluids, and tissue; approved guideline. NCCLS Document M29-A VIIIanova (PA): NCCLS; 1997 December 90p; Federal Occupational Safety and Health Administration. Bloodborne Pathogens Standard, 29 CFR 1910. 1030). Immediately, clean up any spills suspected of potentially containing infectious agents with 0.5% w/v sodium hypochlorite (10% v/v bleach). Dispose of all specimens and materials coming into contact with specimens as though they contain infectious agents. In the event that materials known or suspected of containing infectious agents are ingested or come in contact with open lacerations, lesions, or mucous membranes (eyes, nasal passages, etc.), consult a physician immediately.

Example 2

Sample Preparation Using the Device Kit

The sample preparation steps were performed within a biological safety cabinet using sterile technique and universal precautions relating to the handling of potentially infectious materials. Before beginning the sample preparation process, the protocol of using the device kit that is illustrated in FIGS. 1A & 1B should be familiarized.

Before loading a sample liquid suspension of biological specimen containing analytes of interest, the cap from the device container was unscrewed, inverted and placed on a clean working surface with the absorbent matrix facing upwards (See FIGS. 1A & 1B). About up to 1 ml of sample fluid was slowly added to the top of the matrix plug and allowed it to fully absorb into the matrix. The device kit matrix loaded with the sample fluid was allowed to air-dry. In general, air-drying within a biological safety cabinet takes approximately 4.5 to 5 hours. Once the sample is completely dry, the cap holding the dried specimen-containing matrix was carefully reattached back to the device kit container tube. The specimen is now ready for shipment or storage at ambient temperature.

Example 3

Sample Recovery Using the Device Kit

The sample recovery steps were also performed within a biological safety cabinet using sterile technique and universal precautions relating to the handling of potentially infectious materials. Basically, a sterile 3 or 5 ml disposable Luer-Lok™ syringe (provided by the kit) was inserted into a 15 ml collection tube (also provided by the kit). The plunger was removed from the syringe barrel. The absorbent matrix containing the dried specimen was transferred into the syringe barrel by pressing the matrix against the sterile inside of the syringe barrel's mouth with just enough pressure to break it free from the attached cap and allow it to fall freely to the bottom of the syringe (See FIGS. 4 & 5). The syringe barrel with detached matrix plug was placed into a 15 ml conical collection tube, which is further placed into a rack. About 1 ml of Reconstitution Buffer (supplied by the kit) was applied slowly and directly to the top of the matrix plug to gently re-hydrate the dried specimen absorbed inside the matrix (See FIG. 6). It is necessary to inspect the absorption rate and adjust the application speed as needed while adding the reconstitution buffer, and try not to allow buffer to collect at the bottom of the syringe without first being absorbed into the matrix because failing to fully absorb the reconstitution buffer may result in lower recovery yields. The re-hydrating specimen was allowed to incubate for at least 10 minutes at room temperature prior to adding an additional 175 µl of Reconstitution Buffer to the top of the matrix plug.

The syringe plunger was re-inserted into the syringe barrel and depressed with firm even pressure until the plunger has completely compressed the matrix plug and a maximum volume of approximately 1 ml is collected inside the 15 ml collection tube (See FIGS. 7A, 7B, 7C, & 7D). The syringe barrel, the plunger and the compressed matrix plug were then removed from the 15 ml collection tube and discarded into an appropriate waste receptacle. The 15 ml collection tube containing the newly recovered specimen was sealed with the provided screw cap. The reconstituted sample is ready for storage, testing, or further subsequent analysis.

Example 4

TRUGENE HIV-1 Genotyping Assays Using Reconstituted Sample from the Device Kit The device kit collection performance characteristics were examined, compared, and established with highly character-ized samples using clonal analysis and polymorphic fingerprinting tools. For example, HIV Genotyping results were obtained using RNAs extracted from a 1 ml volume of reconstituted plasma from a device kit stored for 1 day and 7 days, respectively. All extractions were performed using the QIAGEN QIAamp Viral RNA Mini Kit, known in the art. All genotyping assays were performed using the BAYER TRUGENE HIV-1 Genotyping Kit and OpenGene DNA Sequencing System, also known in the art. The device kit HIV Genotyping results were compared with that obtained from frozen plasma, and the summary of genotyping results for both HIV and HIV/HCV coinfected samples were shown in Tables 1(A), 1(B), 1(C), 2(A), 2(B), and 2(C).

TABLE 1(A)

TRUGENE HIV-1 (MT1-SC2-R0001, 100,000 HIV copies/ml)

|  | Frozen Plasma | Device Kit Day 1 | Device Kit day 7 |
|---|---|---|---|
| Protease Region | | | |
| 109 | S37N* | S37N* | S37N* |
| 121 | R41K* | R41K* | R41K* |
| 178 | D60E* | D60E* | D60E* |
| 184 | I62V* | I62V* | I62V* |
| 187 | L63P# | L63P# | L63P# |
| 214 | I72M* | I72M* | I72M* |
| 229 | V77I* | V77I* | V77I* |
| Reverse Transcriptase Region | | | |
| 247 | R83K* | R83K* | R83K* |
| 361 | D121A* | D121A* | D121A* |
| 367 | D123E* | D123E* | D123E* |
| 403 | I135V* | I135V* | I135V* |
| 604 | I202V* | I202V* | I202V* |

*represents polymorphism;
represents resistance mutation

TABLE 1(B)

TRUGENE HIV-1 (MT1-AS2-R0001, 64,700 HIV copies/ml)

|  | Frozen Plasma | Device Kit Day 1 | Device Kit day 7 |
|---|---|---|---|
| Protease Region | | | |
| 28 | L10I# | L10I# | L10I# |
| 37 | I13V* | I13V* | I13V* |
| 94 | V32I# | V32I# | V32I# |
| 97 | L33F# | L33F# | L33F# |
| 109 | S37N* | S37N* | S37N* |
| 136 | M46L# | M46L# | M46L# |
| 160 | I54V# | I54V# | I54V# |
| 187 | L63P# | L63P# | L63P# |
| 211 | A71V# | A71V# | A71V# |
| 229 | V77I* | V77I* | V77I* |
| 244 | V82A# | V82A# | V82A# |
| 268 | L90M# | L90M# | L90M# |
| Reverse Transcriptase Region | | | |
| 121 | M41L# | M41L# | M41L# |
| 127 | K43E* | K43E* | K43E* |
| 130 | E44D# | E44D# | E44D# |
| 199 | D67N# | D67N# | D67N# |
| 205 | T69D# | T69D# | T69D# |
| 247 | R83K* | R83K* | R83K* |
| 352 | V118I# | V118I# | V118I# |
| 367 | D123N* | D123N* | D123N* |
| 412 | E138G* | E138G* | E138G* |

TABLE 1(B)-continued

TRUGENE HIV-1 (MT1-AS2-R0001, 64,700 HIV copies/ml)

|  | Frozen Plasma | Device Kit Day 1 | Device Kit day 7 |
|---|---|---|---|
| 586 | G196E* | G196E* | G196E* |
| 628 | L210W# | L210W# | L210W# |
| 640 | L214F* | L214F* | L214F* |
| 643 | T215Y# | T215Y# | T215Y# |
| 709 | D237E* | D237E* | D237E* |

*represents polymorphism;
represents resistance mutation

TABLE 1(C)

TRUGENE HIV-1 (MT1-GL1-R0001, 24,792 HIV copies/ml)

|  | Frozen Plasma | Device Kit Day 1 | Device Kit day 7 |
|---|---|---|---|
| Protease Region | | | |
| 28 | L10I# | L10I# | L10I# |
| 31 | V11L* | V11L* | V11L* |
| 37 | I13V* | I13V* | I13V* |
| 40 | K14N* | K14N* | K14N* |
| 97 | L33F# | L33F# | L33F# |
| 109 | S37N* | S37N* | S37N* |
| 160 | I54M# | I54M# | I54M# |
| 184 | I62I/V* | I62I/V* | I62I/V* |
| 187 | L63P* | L63P* | L63P* |
| 211 | A71V# | A71V# | A71V# |
| 217 | G73S# | G73S# | G73S# |
| 229 | V77I/V* | V77I/V* | V77I/V* |
| 250 | I84V# | I84V# | I84V# |
| 265 | L89V* | L89V* | L89V* |
| 268 | L90M# | L90M# | L90M# |
| Reverse Transcriptase Region | | | |
| 121 | M41L# | M41L# | M41L# |
| 127 | K43Q* | K43Q* | K43Q* |
| 220 | L74V# | L74V# | L74V# |
| 364 | E122K/E* | E122K/E* | E122K/E* |
| 367 | D123E/D* | D123E/D* | D123E/D* |
| 403 | I135T* | I135T* | I135T* |
| 484 | S162H* | S162H* | S162H* |
| 529 | D177D/G* | D177D/G* | D177D/G* |
| 532 | I178I/M* | I178I/M* | I178I/M* |
| 550 | M184V# | M184V# | M184V# |
| 628 | L210W# | L210W# | L210W# |
| 631 | R211K* | R211K* | R211K* |
| 640 | L214F* | L214F* | L214F* |
| 643 | T215Y* | T215Y* | T215Y* |
| 682 | L228H# | L228H# | L228H# |

*represents polymorphism;
represents resistance mutation

TABLE 2(A)

|  | TRUGENE HIV-1 | | HIV-1 GeneTanker | |
|---|---|---|---|---|
|  | Frozen Plasma | Sample Tanker day 7 | Frozen Plasma | Sample Tanker day 7 |
| Protease Region | | | | |
| 43 | I15V* | I15V* | I15V* | I15V* |
| 103 | E35E/D* | E35D* | E35D* | E35D* |
| 106 | M36I/L# | M36I# | M36I# | M36I# |
| 109 | S37N/S* | S37N* | S37N* | S37N* |
| 169 | R57K* | R57K* | R57K* | R57K* |
| 184 | I62I/V* | I62I/V* | I62V* | I62V* |
| 187 | L63A++ | L63A++ | L63A++ | L63A++ |

TABLE 2(A)-continued

|  | TRUGENE HIV-1 | | HIV-1 GeneTanker | |
|---|---|---|---|---|
|  | Frozen Plasma | Sample Tanker day 7 | Frozen Plasma | Sample Tanker day 7 |
| Reverse Transcriptase Region | | | | |
| 190 | K64R* | K64R* | K64R* | K64R* |
| 364 | E122K/E* | E122K/E* | E122K/E* | E122K/E* |
| 403 | I135T* | I135T* | I135T* | I135T* |
| 631 | R211K* | R211K/R* | R211K* | R211K* |
| 640 | L214F* | L214F* | L214F* | L214F* |
| 733 | V245E* | V245E* | X | X |

*represents polymorphism;
represents resistance mutation;
++represents unexpected mutation

TABLE 2(B)

|  | TruGene HIV-1 | | HIV-1 GeneTanker | |
|---|---|---|---|---|
|  | Frozen Plasma | Sample Tanker day 7 | Frozen Plasma | Sample Tanker day 7 |
| Protease Region | | | | |
| 103 | E35D* | E35D* | E35D* | E35D* |
| 109 | S37N* | S37N* | S37N* | S37N* |
| 229 | V77I/V* | V77I/V* | V77I/V* | V77I/V* |
| Reverse Transcriptase Region | | | | |
| 301 | K101K/E# | K101K/E# | K101K/E# | K101K/E# |
| 316 | V106A/V# | V106A/V# | V106A/V# | V106A/V# |
| 364 | E122K* | E122K* | E122K* | E122K* |
| 631 | R211K* | R211K* | R211K* | R211K* |
| 640 | L214F* | L214F* | L214F* | L214F* |
| 643 | T215Y# | T215Y# | T215Y# | T215Y# |
| 733 | V245K* | V245K* | X | X |

*represents polymorphism;
represents resistance mutation

TABLE 2(C)

|  | TruGene HIV-1 | | HIV-1 GeneTanker | |
|---|---|---|---|---|
|  | Frozen Plasma | Sample Tanker day 7 | Frozen Plasma | Sample Tanker day 7 |
| Protease Region | | | | |
| 43 | I15V* | I15V* | I15V* | I15V* |
| 103 | E35D* | E35D* | E35D* | E35D* |
| 106 | M36I# | M36I# | M36I# | M36I# |
| 109 | S37D* | S37D* | S37D* | S37D* |
| 169 | R57K/R* | R57K* | R57K* | R57K* |
| Reverse Transcriptase Region | | | | |
| 121 | M41L# | M41L# | M41L# | M41L# |
| 127 | K43K/T* | K43K/T* | K43K/T* | K43N* |
| 130 | E44E/D# | E44E/D# | E44E/D# | E44D# |
| 199 | D67N# | D67N# | D67N# | D67N# |
| 367 | D123N* | D123N* | D123N* | D123N* |
| 586 | X | G196E/G* | X | G196E/G* |
| 619 | Q207E* | Q207E* | Q207E* | Q207E* |
| 628 | L210W# | L210W# | L210W# | L210W# |
| 631 | R211K* | R211K* | R211K* | R211K* |

TABLE 2(C)-continued

|  | TruGene HIV-1 | | HIV-1 GeneTanker | |
|---|---|---|---|---|
|  | Frozen Plasma | Sample Tanker day 7 | Frozen Plasma | Sample Tanker day 7 |
| 640 | L214F* | L214F* | L214F* | L214F* |
| 643 | T215Y# | T215Y# | T215Y# | T215Y# |

*represents polymorphism;
represents resistance mutation

The data in Tables 1(A), 1(B), 1(C), 2(A), 2(B), and 2(C) indicate that the reconstituted samples from device kit stored at ambient temperature for 1 and 7 days prior to testing showed no subsequent degradation of peak intensity or increased signal to noise ratio. The reconstituted samples from device kit showed a high degree of correlation and reproducibility to that of standard frozen plasma samples.

Example 5

Bayer Versant HIV-1 RNA 3.0 Assay (bDNA) Using Reconstituted Samples from the Device Kit In this study, the reconstituted samples from device kit collection were stored dry at ambient temperature for 1 day prior to testing. The Bayer Versant HIV-1 RNA 3.0 Assay is known in the art. The data shown in Table 3 indicate the reproducibility using samples from the device kit.

TABLE 3

| Description | RNA copies/mL | RNA $Log_{10}$ | Mean RNA $Log_{10}$ | $Log_{10}$ Variance | Mean $Log_{10}$ Variance* |
|---|---|---|---|---|---|
| Device Kit | 43,480 | 4.64 | 4.58 | 0.06 | 0.03 |
| Device Kit | 34,285 | 4.54 | 4.58 | 0.04 | 0.03 |
| Device Kit | 39,085 | 4.59 | 4.58 | 0.01 | 0.03 |
| Device Kit | 37,751 | 4.58 | 4.58 | 0 | 0.03 |
| Device Kit | 35,298 | 4.55 | 4.58 | 0.03 | 0.03 |
| Device Kit | 40,005 | 4.6 | 4.58 | 0.02 | 0.03 |
| Device Kit | 5,439 | 3.74 | 3.76 | 0.02 | 0.04 |
| Device Kit | 5,295 | 3.72 | 3.76 | 0.04 | 0.04 |
| Device Kit | 5,150 | 3.71 | 3.76 | 0.05 | 0.04 |
| Device Kit | 6,142 | 3.79 | 3.76 | 0.03 | 0.04 |
| Device Kit | 6,611 | 3.82 | 3.76 | 0.06 | 0.04 |
| Device Kit | 5,905 | 3.77 | 3.76 | 0.01 | 0.04 |
| Device Kit | 726 | 2.86 | 2.75 | 0.11 | 0.07 |
| Device Kit | 522 | 2.72 | 2.75 | 0.03 | 0.07 |
| Device Kit | 710 | 2.85 | 2.75 | 0.1 | 0.07 |
| Device Kit | 417 | 2.62 | 2.75 | 0.13 | 0.07 |
| Device Kit | 568 | 2.75 | 2.75 | 0 | 0.07 |
| Device Kit | 476 | 2.68 | 2.75 | 0.07 | 0.07 |

Example 6

Roche UltraSensitive AMPLICOR HIV-1 MONITOR Test, Version 1.5 for Quantifying Viral Load Using Reconstituted Samples from the Device Kit In this study, the reconstituted samples from the device kit collection were stored dry at ambient temperature for 7 days prior to testing. The Roche UltraSensitive AMPLICOR HIV-1 MONITOR Test v 1.5 is known in the art and was performed using samples reconstituted from the device kit dried EDTA plasma. The data shown in Table 4 indicate the reproducibility using samples from the device kit.

TABLE 4

| Sample Type | Copies/mL | $LOG_{10}$ | $LOG_{10}$ Mean | $LOG_{10}$ Variance | $LOG_{10}$ Mean Variance |
|---|---|---|---|---|---|
| Dried EDTA Plasma | 3,861 | 3.59 | 3.6 | 0.01 | 0.01 |
| Dried EDTA Plasma | 4,060 | 3.61 | 3.6 | 0.01 | 0.01 |
| Dried EDTA Plasma | 4,085 | 3.61 | 3.6 | 0.01 | 0.01 |
| Dried EDTA Plasma | 14,640 | 4.17 | 4.04 | 0.13 | 0.09 |
| Dried EDTA Plasma | 9,314 | 3.97 | 4.04 | 0.07 | 0.09 |
| Dried EDTA Plasma | 9,249 | 3.97 | 4.04 | 0.07 | 0.09 |
| Dried EDTA Plasma | 19,981 | 4.3 | 4.28 | 0.02 | 0.03 |
| Dried EDTA Plasma | 19,816 | 4.3 | 4.28 | 0.02 | 0.03 |
| Dried EDTA Plasma | 16,788 | 4.23 | 4.28 | 0.05 | 0.03 |
| Dried EDTA Plasma | 21,757 | 4.34 | 4.44 | 0.1 | 0.09 |
| Dried EDTA Plasma | 25,155 | 4.4 | 4.44 | 0.04 | 0.09 |
| Dried EDTA Plasma | 37,087 | 4.57 | 4.44 | 0.13 | 0.09 |
| Dried EDTA Plasma | 1,275 | 3.11 | 3.19 | 0.08 | 0.05 |
| Dried EDTA Plasma | 1,837 | 3.26 | 3.19 | 0.07 | 0.05 |
| Dried EDTA Plasma | 1,590 | 3.2 | 3.19 | 0.01 | 0.05 |
| Dried EDTA Plasma | 1,037 | 3.02 | 3.04 | 0.02 | 0.05 |
| Dried EDTA Plasa | 981 | 2.99 | 3.04 | 0.05 | 0.05 |
| Dried EDTA Plasma | 1,274 | 3.11 | 3.04 | 0.07 | 0.05 |

OVERALL LOG10 Mean Variance = 0.05
Device Kit specimens were stored dry at ambient temperature for 7 days prior to testing.
N = 18 (6 samples × 3 replicates each)

Example 7

TRUGENE HCV 5'NC Genotyping Assays Using Reconstituted Samples from the Device Kit In this study, the HCV 5'NC genotypes were obtained from RNA extracted from 140 µl of a 1.0 ml volume of thawed or reconstituted plasma. RNA was extracted using the QIAGEN QIAamp Viral RNA Mini Kit, known in the art. All genotyping assays were performed using the BAYER TRUGENE HCV 5'NC Genotyping Kit and OpenGene DNA Sequencing System, also known in the art. The device kit HCV 5'NC Genotyping results were compared with that obtained from frozen plasma, and the summary of genotyping results for HIV/HCV coinfected samples is shown in Tables 5(A), 5(B), and 5(C).

TABLE 5(A)

| Co-Infected Sample #1 | |
|---|---|
| From Frozen Plasma | Filter Matrix d7 Post Prep |
| Genotype: 2b | Genotype: 2b |

TABLE 5(B)

| Co-Infected Sample #1 | |
|---|---|
| From Frozen Plasma | Filter Matrix d7 Post Prep |
| Genotype: 3 | Genotype: 3a |

TABLE 5(C)

| Co-Infected Sample #1 | |
|---|---|
| From Frozen Plasma | Filter Matrix d7 Post Prep |
| Genotype: 1a | Genotype: 1a |

Example 8

Comparison of Viral Load and Resistance Genotyping Between Frozen Plasma and a Novel Dried Plasma Transportation Medium (Device Kit) on Treated Patient Samples Methods:

Viral load, RNA extraction, and genotyping: HIV-1 viral loads were determined using either the Standard or UltraSensitive AMPLICOR HIV-1 MONITOR® Test v 1.5 (Roche Diagnostics, Indianapolis, Ind.), VERSANT® HIV-1 RNA 3.0 Assay (bDNA) (Bayer Healthcare, Tarrytown, N.Y.) or NucliSens® HIV-1 QT Assay (bioMerieux, Durham, N.C.). Total viral RNA for all samples used in genotyping were extracted using the QIAamp® Viral RNA Mini Kit (Qiagen, Valencia, Calif.). HIV-1 genotype was determined using either or both the TRUGENE® HIV-1 Genotyping Kit (Bayer Healthcare) and the HIV-1 GeneTanker Genotyping Complete Assay (Research Think Tank, Inc). The HCV genotype was determined using the TRUGENE HCV 5'NC Genotyping Kit (Bayer Healthcare). All sequencing, data processing and reporting were performed using the OpenGene® DNA Sequencing System (Bayer Healthcare).

The device matrix (FIGS. 1A and 1B) has a maximum capacity of 1 mL. A 1 mL volume of plasma was added to each matrix, allowed to air-dry in a biosafety cabinet for 4-5 hours, then packaged in the device kit tube and stored or shipped at ambient temperature. Dried sample matrices were re-hydrated with the appropriate volume of Reconstitution Buffer to recover 1 mL of reconstituted plasma.

Amplicor viral load intra-assay reproducibility using the device kit: three matrices were prepared for each of six randomly selected HIV-1 positive plasma samples (N=18). The matrix specimens were reconstituted and recovered on day 7 post preparation and were used to examine the intra-assay viral load reproducibility of the UltraSensitive AMPLICOR viral load assay.

Versant viral load intra-assay reproducibility using the device kit: six matrices were prepared for each of three serial dilutions from an HIV-1 positive sample (N=18). The matrix specimens were reconstituted and recovered on day 1 post preparation and were used to examine the intra-assay viral load reproducibility of the Versant viral load assay.

NucliSens viral load intra-assay reproducibility using the device kit: five matrices were prepared for each of three randomly selected HIV-1 positive plasma samples (N=15). The matrix specimens were reconstituted and recovered on day 3.5 post preparation and were used to examine the intra-assay viral load reproducibility of the NucliSens viral load assay.

HIV-1 genotyping stability: Three archived HIV-1 positive plasma samples with previously determined viral-loads were randomly selected to prepare the device matrices for genotype stability testing. Two identical sets of matrices were prepared for each sample following the method described above. The dry packaged matrices were stored at ambient temperature for up to 7 days. Reconstituted plasma for each set of matrices was recovered on either day 1 or day 7, respectively. For each sample the entire recovered volume was extracted. Genotyping was performed on all samples using the TRUGENE HIV-1 genotyping kit, following the manufacturer's protocol. The matrix genotypes were then compared with previously determined frozen plasma-derived genotypes.

HIV-1/HCV co-infection: For each of three HIV-1/HCV co-infected plasma samples, a single matrix and frozen plasma aliquot were prepared by an external laboratory and shipped overnight to Research Think Tank. The plasma aliquots were shipped on dry ice, while the device kit specimens were shipped separately at ambient temperature. Upon receipt, the matrix specimens were stored at ambient temperature until reconstituted for testing on day 7 post preparation. The corresponding frozen plasma were thawed for testing in parallel on day 7. All samples were assayed for viral load in duplicate using the Standard AMPLICOR viral load assay. A 140 µL volume of each sample was extracted for total RNA (HIV-1 and HCV), then genotyped using the TRUGENE HIV-1, the HIV-1 GeneTanker and the HCV TRUGENE HCV 5'NC kits, following manufacturer's protocol.

Phenotyping:

RNA extracted from matched The device kit and frozen plasma HIV-1/HCV co-infected specimens were submitted for Phenoscript™ (VIRalliance, Paris, France) phenotyping analysis.

Results:

Device Kit Characteristics:

The device kit consisted of an absorbent fibrous matrix for the preparation of dried plasma specimens and a desiccant storage/transportation tube. The matrix yielded an approximate recovered plasma volume of 1.035+/−0.03 mL. The device kit specimens were dried in a biosafety cabinet, at ambient temperature, for a minimum of 4.5 hours prior to packaging. Viral load assays: The mean $\log_{10}$ difference between matched frozen and the device kit dried plasma specimens using the standard AMPLICOR HIV-1 and VERSANT HIV-1 assay was 0.36 and 0.51, respectively (Table 6A and B; Standard Roche viral load for 9 randomly selected specimens and Bayer bDNA HIV-1 viral load for 12 randomly selected specimens respectively). Intra-assay quantitative reproducibility experiments for device kit indicated an overall $\text{Log}_{10}$ mean variance of 0.05 for the UltraSensitive AMPLICOR HIV-1 assay at day 7 (Table 4), 0.05 for the VERSANT HIV-1 assay at day 1 (Table 3) and 0.06 for the NucliSens HIV-1 QT assay at day 3.5 (Table 7). Viral load values obtained from the device kit specimens were consistently lower than those obtained from matched frozen plasma specimens.

Genotyping Assays:

The sequence quality generated between matched the device kit and frozen plasma specimens was comparable. However, in several sequences the device kit specimens exhibited an increase in sequence quality (data not shown). Mutation profiles obtained using either the TRUGENE HIV-1 and/or HIV-1 GeneTanker genotyping kits exhibited a high degree of concordance between matched the device kit and frozen plasma specimens (Table 1 and 2). This concordance was consistent regardless of HIV-1 viral-load, storage time or shipping conditions prior to genotype testing. Among matched co-infected the device kit and frozen plasma specimens, there was a 100% concordance at the genotype level for HCV using the TRUGENE HCV 5'NC kit. While samples 37 and 39 were in agreement at the subtype level, HCV subtype was unable to be determined for the sample 38 plasma specimens.

Phenotyping:

Phenotype results were successfully obtained for all matched HIV-1/HCV co-infected The device kit and frozen plasma specimens.

TABLE 6A

| Sample | Description | RNA Copies/mL | RNA Log10 | Log10 Difference |
|---|---|---|---|---|
| 1 | Plasma | 23,15 | 4.3 | 0.4 |
|   | Device Kit | 7,87 | 3.9 |   |
| 2 | Plasma | 544,25 | 5.7 | 0.3 |
|   | Device Kit | 231,24 | 5.3 |   |
| 3 | Plasma | 33,17 | 4.5 | 0.2 |
|   | Device Kit | 20,36 | 4.3 |   |
| 4 | Plasma | 4,10 | 3.6 | 0.2 |
|   | Device Kit | 2,49 | 3.4 |   |
| 5 | Plasma | 394,70 | 5.6 | 0.5 |
|   | Device Kit | 106,41 | 5.0 |   |
| 6 | Plasma | 130,54 | 5.1 | 0.3 |
|   | Device Kit | 54,63 | 4.7 |   |
| 7 | Plasma | 11,28 | 4.0 | 0.2 |
|   | Device Kit | 6,53 | 3.8 |   |
| 8 | Plasma | 601,85 | 5.7 | 0.1 |
|   | Device Kit | 397,27 | 5.6 |   |
| 9 | Plasma | 4,73 | 3.6 | 0.6 |
|   | Device Kit | 1,15 | 3.0 |   |

TABLE 6B

| Sample | Description | RNA Copies/mL | RNA Log10 | Log10 Difference |
|---|---|---|---|---|
| 1 | Plasma | 18,20 | 4.2 | 0.5 |
|   | Device Kit | 4,88 | 3.6 |   |
| 1 | Plasma | 49,22 | 4.6 | 0.4 |
|   | Device Kit | 16,55 | 4.2 |   |
| 1 | Plasma | <7 | NA | NA |
|   | Device Kit | <7 | NA |   |
| 1 | Plasma | <7 | NA | NA |
|   | Device Kit | <7 | NA |   |
| 1 | Plasma | <7 | NA | NA |
|   | Device Kit | <7 | NA |   |
| 1 | Plasma | 458,60 | 5.6 | 0.3 |
|   | Device Kit | 224,34 | 5.3 |   |
| 1 | Plasma | 41 | 2.6 | 0.6 |
|   | Device Kit | 10 | 2.0 |   |
| 1 | Plasma | 26,11 | 4.4 | 0.5 |
|   | Device Kit | 7,86 | 3.9 |   |
| 1 | Plasma | 40,85 | 4.6 | 0.5 |
|   | Device Kit | 12,05 | 4.0 |   |
| 1 | Plasma | 2,08 | 3.3 | 0.7 |
|   | Device Kit | 37 | 2.5 |   |
| 2 | Plasma | 225,36 | 5.3 | 0.4 |
|   | Device Kit | 88,64 | 4.9 |   |
| 2 | Plasma | 32,48 | 4.5 | 0.4 |
|   | Device Kit | 11,19 | 4.0 |   |

TABLE 7

| Sample | Description | RNA Copies/m | RNA Log$_{10}$ | Mean RNA Log$_{10}$ | Mean Log$_{10}$ Variance* |
|---|---|---|---|---|---|
| 3 | Device Kit | 87 | 2.9 | 2.8 | 0.0 |
|   | Device Kit | 64 | 2.8 |   |   |
|   | Device Kit | 52 | 2.7 |   |   |
|   | Device Kit | 59 | 2.7 |   |   |
|   | Device Kit | 81 | 2.9 |   |   |
|   | Device Kit |   |   |   |   |
| 3 | Device Kit | 16,70 | 4.2 | 4.2 | 0.0 |
|   | Device Kit | 21,50 | 4.3 |   |   |
|   | Device Kit | 19,05 | 4.2 |   |   |
|   | Device Kit | 19,55 | 4.2 |   |   |
|   | Device Kit | 22,37 | 4.3 |   |   |
|   | Device Kit |   |   |   |   |
| 3 | Device Kit | 130,00 | 5.1 | 5.0 | 0.0 |
|   | Device Kit | 110,50 | 5.0 |   |   |
|   | Device Kit | 95,00 | 4.9 |   |   |
|   | Device Kit | 120,00 | 5.0 |   |   |
|   | Device Kit | 138,00 | 5.1 |   |   |

We claim:

1. A method for recovering a dried biological specimen comprising:
   (a) providing a dried biological specimen contained on an absorbent three dimensional matrix in a sealed container, wherein the matrix has an absorption capacity of at least 0.1 ml;
   (b) exposing the matrix by opening the container;
   (c) selecting a fixed volume of a reconstitution buffer;
   (d) applying the fixed volume of the reconstitution buffer to the matrix containing the dried biological specimen, thereby forming a reconstituted biological specimen contained on the matrix, wherein the fixed volume of the reconstitution buffer is less than the absorption capacity of the matrix; and
   (e) removing the reconstituted biological specimen from the matrix.

2. The method of claim 1, wherein the absorption capacity of the matrix is at least 0.5 ml.

3. The method of claim 1, wherein the absorption capacity of the matrix is at least 1.0 ml.

4. The method of claim 1, wherein the matrix is at least 50% porous.

5. The method of claim 1, wherein the matrix is at least 75% porous.

6. The method of claim 1, wherein the container comprises an openable lid, and wherein exposing the matrix by opening the container comprises opening the lid.

7. The method of claim 6, wherein the lid comprises an internal surface lid extension, and wherein the matrix is removably mounted to the lid via the internal surface lid extension.

8. The method of claim 1, wherein removing the reconstituted biological specimen from the matrix comprises compressing the matrix.

9. The method of claim 8, wherein the matrix is compressed by at least 50% of a volume of the matrix.

10. The method of claim 8, wherein the matrix is compressed by at least 75% of a volume of the matrix.

11. The method of claim 1, wherein removing the reconstituted biological specimen from the matrix comprises centrifuging the matrix.

12. The method of claim 1, wherein the fixed volume of the reconstitution buffer is less than or equal to a sample volume of at least 0.1 ml of a biological specimen previously absorbed and dried on the matrix to form the dried biological specimen.

13. The method of claim 1, wherein the fixed volume of the reconstitution buffer is less than a sample volume of at least 0.1 ml of a biological specimen previously absorbed and dried on the matrix to form the dried biological specimen.

14. The method of claim 1, wherein the biological specimen contains an analyte of interest selected from the group consisting of nucleic acids, proteins, carbohydrates, lipids, whole cells, cellular fragments, whole virus and viral fragments.

15. The method of claim 1, wherein the biological specimen contains an analyte of interest selected from the group consisting of DNA and RNA.

16. The method of claim 1, wherein the biological specimen is selected from the group consisting of whole blood, plasma, serum, lymph, synovial fluid, urine, saliva, sputum, semen, vaginal lavage, bone marrow, cerebrospinal cord fluid, physiological body liquids, pathological body liquids, and combinations thereof.

17. A method for recovering a dried biological specimen comprising:
   (a) providing a dried biological specimen contained on an absorbent three dimensional matrix, wherein the matrix has an absorption capacity of at least 0.1 ml;
   (b) selecting a fixed volume of a reconstitution buffer;
   (c) reconstituting the dried biological specimen on the matrix with the fixed volume of the reconstitution buffer, thereby forming a reconstituted biological specimen contained on the matrix, wherein the fixed volume of the reconstitution buffer is less than the absorption capacity of the matrix; and
   (d) removing the reconstituted biological specimen from the matrix.

18. The method of claim 17, wherein the fixed volume of the reconstitution buffer is less than or equal to a sample volume of at least 0.1 ml of a biological specimen previously absorbed and dried on the matrix to form the dried biological specimen.

19. The method of claim 17, wherein the fixed volume of the reconstitution buffer is less than a sample volume of at least 0.1 ml of a biological specimen previously absorbed and dried on the matrix to form the dried biological specimen.

20. The method of claim 17, wherein the biological specimen contains an analyte of interest selected from the group consisting of nucleic acids, proteins, carbohydrates, lipids, whole cells, cellular fragments, whole virus and viral fragments.

21. The method of claim 17, wherein the biological specimen contains an analyte of interest selected from the group consisting of DNA and RNA.

22. A method for recovering a dried biological specimen comprising:
   (a) providing a dried biological specimen contained on an absorbent three dimensional matrix sealed in a container, wherein the matrix has an absorption capacity of at least 0.1 ml;
   (b) exposing the matrix by opening the container;
   (c) selecting a fixed volume of a reconstitution buffer;
   (d) applying the fixed volume of the reconstitution buffer to the matrix containing the dried biological specimen, thereby forming a reconstituted biological specimen contained on the matrix, wherein the fixed volume of the reconstitution buffer is less than or equal to a sample volume of at least 0.1 ml of a biological specimen previously absorbed and dried on the matrix to form the dried biological specimen; and
   (e) removing the reconstituted biological specimen from the matrix.

23. The method of claim 22, wherein the fixed volume of the reconstitution buffer is less than the sample volume of the biological specimen.

24. The method of claim 22, wherein the fixed volume of the reconstitution buffer is less than the absorption capacity of the matrix.

25. The method of claim 22, wherein the biological specimen contains an analyte of interest selected from the group consisting of nucleic acids, proteins, carbohydrates, lipids, whole cells, cellular fragments, whole virus and viral fragments.

26. The method of claim 22, wherein the biological specimen contains an analyte of interest selected from the group consisting of DNA and RNA.

* * * * *